US007399614B2

(12) United States Patent
Zon

(10) Patent No.: US 7,399,614 B2
(45) Date of Patent: Jul. 15, 2008

(54) 5-METHYLCYTOSINE DETECTION, COMPOSITIONS AND METHODS THEREFOR

(75) Inventor: Gerald Zon, San Carlos, CA (US)

(73) Assignee: Applera Corporation, Foster City, CA (US)

( * ) Notice: Subject to any disclaimer, the term of this patent is extended or adjusted under 35 U.S.C. 154(b) by 203 days.

(21) Appl. No.: 10/881,363

(22) Filed: Jun. 30, 2004

(65) Prior Publication Data

US 2006/0172309 A1    Aug. 3, 2006

(51) Int. Cl.
*C12P 19/34* (2006.01)
*C12Q 1/68* (2006.01)
*C07H 21/02* (2006.01)
*C07H 21/04* (2006.01)
*C07H 19/04* (2006.01)

(52) U.S. Cl. .................. 435/91.1; 435/6; 435/91.2; 536/23.1; 536/24.3; 536/24.33; 536/26.6

(58) Field of Classification Search .......... 435/6, 435/91.1, 91.2; 536/23.1, 24.3, 24.33, 26.6
See application file for complete search history.

(56) References Cited

U.S. PATENT DOCUMENTS

| | | | |
|---|---|---|---|
| 5,210,015 | A | 5/1993 | Gelfand et al. |
| 5,436,149 | A | 7/1995 | Barnes |
| 6,210,891 | B1 | 4/2001 | Nyren |
| 6,258,568 | B1 | 7/2001 | Nyren |
| 7,118,868 | B2 * | 10/2006 | Berlin ........................ 435/6 |

FOREIGN PATENT DOCUMENTS

WO    WO 90/01069    2/1990

OTHER PUBLICATIONS

Royer, R. E. et al.; "Reactivity-Selectivity Properties of Reactions of Carcinogenic Electrophiles with Biomolecules;" Journal of Organic Chemistry, vol. 44, No. 18 (Aug. 31, 1979); pp. 3202-3207.
Szejnwald, Brown H. et al.; "Preparation and Enzymatic Hydrolysis of Dinucleoside Monophosphates and DNA Modified with Aromatic Residues;" Nucleic Acids and Protein Synthesis, vol. 475, No. 2 (Mar. 18, 1977); pp. 241-253.
Scribner, J. D. et al.; "Adducts Between the Carcinogen 2 Acetamido Phenanthrene and Adenine and Guanine of DNA;" Cancer Research, vol. 35, No. 6 (1975); pp. 1416-1421.
Pochon, F. et al.; "Action of the Carcinogen 7 Bromomethyl Benz Anthracene on Synthetic Poly Nucleotides;" European Journal of Biochemistry, vol. 21, No. 1 (Jul. 1971); pp. 144-153.
Che, Y. et al.; "A Multiplexing Single Nucleotide Polymorphism Typing Method Based on Restriction-Enzyme-Mediated Single-Base Extension and Capillary Electrophoresis;" Analytical Biochemistry, Academic Press, New York, NY, vol. 329, No. 2 (Jun. 15, 2004); pp. 220-229.
Rein et al.; "Identifying 5-Methylcytosine and Related Modifications in DNA Genomes;" Nucleic Acids Research, Oxford University Press, vol. 26, No. 10 (May 15, 1998); pp. 2255-2264.
Balog, Robert P. et al.; "Parallel assessment of CpG methylation by two-color hybridization with oligonucleotide arrays"; Analytical Biochemistry 309 (2002) 301-310.
Benhattar, Jean et al.; "Methylation-Sensitive Single-Strand Conformation Analysis"; Methods in Molecular Biology, vol. 287, pp. 181-193; Epigenetics Protocols; Edited by: T.O. Tollefsbol.
Colasanti, Joseph et al.; "Cytosine Methylated DNA synthesized by Taq polymerase used to assay methylation sensitivity of restriction endonuclease Hinfl"; Nucleic Acids Research; (Dec. 4, 1990); vol. 19, No. 2; pp. 391-394.
Cook, Lindsey et al.; "Methylated DNA labels for marking objects"; Biotechnology Letters 25: 89-94; (2003).
Cottrell, Susan E.; "A real-time PCR assay for DNA-methylation using methylation-specific blockers"; Nucleic Acids Research; vol. 32, No. 1; 2004; pp. 1-8.
Derks, Sarah et al.; "Methylation-specific PCR unraveled"; Cellular Oncology 26 (2004); pp. 291-299.
Fackler, Mary Jo et al.; "Quantitative Multiplex Methylation-Specific PCR Assay for the Detection of Promoter Hypermethylation in Multiple Genes in Breast Cancer"; Cancer Research 64, 4442-4452, Jul. 1, 2004.
Fraga, Mario F. et al.; "DNA Methylation: A Profile of Methods and Applications"; BioTechniques 33:632-649 (Sep. 2002).
Gitan, Raad S. et al.; "Methylation-Specific Oligonucleotide Microarray: A New Potential for High Throughput Methylation Analysis"; Genome Research; (Sep. 20, 2001) pp. 158-164.
Guldberg, Per et al.; "Profiling DNA methylation by melting analysis"; Methods 27 (2002) 121-127.
Laird, Charles D. et al.; "Hairpin-bisulfite PCR: Assessing epigenetic methylation patterns on complementary strands of individual DNA molecules"; PNAS (Jan. 6, 2004); vol. 101, No. 1; pp. 204-209.
Lewin, Jörn et al.; "Quantitative DNA methylation analysis based on four-dye trace data from direct sequencing of PCR amplificates"; Bioinformatics; vol. 20, No. 17 (2004); pp. 3005-3012.
Li, Long-Cheng; "MethPrimer: designing primers for methylation PCRs"; Bioinformatics; vol. 18, No. 11 (2002); pp. 1427-1431.
Liu, Liang et al.; "Profiling DNA Methylation by Bisulfite Genomic Sequencing"; Methods in Molecular Biology, vol. 287; pp. 169-179; Epigentics Protocols; Edited by Trygve O. Tollefsbol.

(Continued)

*Primary Examiner*—Jezia Riley
(74) *Attorney, Agent, or Firm*—Harness, Dickey & Pierce, P.L.C.

(57) ABSTRACT

Compositions and methods for detecting 5-methylcytosine in a nucleic acid are disclosed. A 5-methylcytosine discriminator, which is a deoxyribonucleosidetriphosphate comprising a cytosine-pairing moiety such as a guanosine and a moiety which hinders hydrogen bonding between the cytosine-pairing moiety and a 5-methylcytosine is described. The discriminator is able to base pair with a cytosine but not a 5-methylcytosine. A 5-methylcytosine comprised by a target nucleotide can be detected in a reaction using a DNA polymerase and a primer hybridized immediately adjacent to the target nucleotide. In the reaction, pyrophosphate released upon incorporation of a dNTP complementary to a target nucleotide is detected. Lack of incorporation of the discriminator, but incorporation of a dGTP, can indicate that the target nucleotide is a 5-methylcytosine.

29 Claims, No Drawings

OTHER PUBLICATIONS

Liu, Ze-Jun et al.; "Polymerase chain reaction-based methods of DNA methylation analysis"; Analytical Biochemestry 317 (2003) 259-265.

Maekawa, Masato et al.; DNA Methylation Analysis Using Bisulfite Treatment and PCR-Single-Strand Conformation Polymorphism in Colorectal Cancer Showing Microsatellite Instability; Biochemical and Biophysical Research Communications 262, 671-676 (1999).

Makrigiorgos, Mike G. et al.; :A PCR-based amplification method retaiing the quantitative differnce between two complex genomes; Nature Biotechnology; vol. 20; Sep. 2002; pp. 936-939.

Nagane, Yuriko et al.; "PCR amplification in bisulfite methylcytosine mapping in the GC-rich promoter region of amyloid precursor protein gene in autopsy human brain"; Brain Research Protocols 5 (2000) 167-171.

Ohashi, Haruhiko; "Methylation-Specific PCR"; Methods in Molecular Biology, vol. 192, pp. 91-97; PCR Cloning Protocols, 2nd Edition; Edited by B-Y Chen and H.W. Janes.

Ohmori, Haruo et al.; "Detection of 5-methylcytosine in DNA sequences"; Nucleic Acids Research; vol. 5, No. 5; (May 1978); pp. 1479-1485.

Panagopoulos, Ioannis et al.; "A Methylation PCR Approach for Detection of Fragile X Syndrome"; Methods; Human Mutation 14: 71-79 (1999).

Sasaki, Masahiro et al.; "Bisulfite conversion-specific and methylation-specific PCR: a sensitive technique for accurate evaluation of CpG methylation"; Biochemical and Biophysical Research Communications 309 (2003) 305-309.

Steigerwald, Sabine D. et al.; "Ligation-mediated PCR improves the sensitivity of methylation analysis by restriction enzymes and detection of specific DNA strand breaks"; Nucleic Acids Research; vol. 18, No. 6; pp. 1435-1439 (Feb. 11, 1990).

Thomassin, Helene et al.; "Identification of 5-Methylcytosine in Complex Genomes"; Methods 19, 465-475 (1999).

Thomassin, Helene et al.; "MethylQuant: a sensitive method for quantifying methylation of specific cytosines within the genome"; Nucleic Acids Research (2004); vol. 32, No. 21; pp. 1-9.

Towers, Greg J. et al; "One Step Screening of Retroviral Producer Clones by Real Time Quantitative PCR"; The Journal of Gene Medicine 1999; 1: 352-359.

Toyota, Minoru et al.; "Identification of Differentialy Methylated Sequences in Colorectal Cancer by Methylated CpG Island Amplification"; Cancer Research 59; May 15, 1999; pp. 2307-2312.

Trinh, Binh N. et al; DNA Methylation Analysis by MethyLight Technology; Methods 25, 456-462 (2001).

Tusnady, Gabor E. et al.; "BiSearch: primer-design and search tool for PCR on bisulfite-treated genomes"; Nucleic Acids Research; vol. 33, No. 1; 2005; pp. 1-6.

van Dijk, Jeroen P. et al.; "A Novel, Essential Control for Clonality Analysis with Human Androgen Receptor Gene Polymerase Chain Reaction"; American Journal of Pathology; vol. 161, No. 3; Sep. 2002; pp. 807-812.

Warnecke, Peter M. et al.; "Detection and measurement of PCR bias in quantitative methylation analysis of bisulphite-treated DNA"; Nucleic Acids Research; vol. 25, No. 21; 1997; pp. 4422-4426.

Worm, Jesper et al.; "In-Tube DNA Methylation Profiling by Fluorescence Melting Curve Analysis"; Clinical Chemistry 47:7; 2001; pp. 1183-1189.

Yang, Allen S.; "A simple method for estimating global DNA methylation using bisulfite PCR of repetitive DNA elements"; Nucleic Acids Research; vol. 32, No. 3; pp. 1-6 (2004).

Zeschnigk, Michael et al.; "A novel real-time PCR assay for quantitative analysis of of methylated alleles (QAMA): analysis of the retinoblastoma locus"; Nucleic Acids Research, 2004; vol. 32, No. 16; pp. 1-5.

* cited by examiner

```
                        SEQUENCE LISTING

<160> NUMBER OF SEQ ID NOS: 7

<210> SEQ ID NO 1
<211> LENGTH: 26
<212> TYPE: DNA
<213> ORGANISM: Human

<400> SEQUENCE: 1
gacgcgataa tattagatcc gacgac                                            26

<210> SEQ ID NO 2
<211> LENGTH: 11
<212> TYPE: DNA
<213> ORGANISM: Human

<400> SEQUENCE: 2
gatccgacga c                                                            11

<210> SEQ ID NO 3
<211> LENGTH: 11
<212> TYPE: DNA
<213> ORGANISM: Artificial
<220> FEATURE:
<223> OTHER INFORMATION: Synthetically derived primer sequence

<400> SEQUENCE: 3
gtcgtcggat c                                                            11

<210> SEQ ID NO 4
<211> LENGTH: 12
<212> TYPE: DNA
```

-continued

```
<213> ORGANISM: Human

<400> SEQUENCE: 4
taatattatc gc                                                           12

<210> SEQ ID NO 5
<211> LENGTH: 22
<212> TYPE: DNA
<213> ORGANISM: Human

<400> SEQUENCE: 5
cgcgcgataa agatccgacg ag                                                22

<210> SEQ ID NO 6
<211> LENGTH: 11
<212> TYPE: DNA
<213> ORGANISM: Human

<400> SEQUENCE: 6
gatccgacga c                                                            11

<210> SEQ ID NO 7
<211> LENGTH: 11
<212> TYPE: DNA
<213> ORGANISM: Artificial
<220> FEATURE:
<223> OTHER INFORMATION: Synthetically derived primer sequence

<400> SEQUENCE: 7
ctcgtcggat c                                                            11
```

5-METHYLCYTOSINE DETECTION, COMPOSITIONS AND METHODS THEREFOR

FIELD

The present invention relates to methods and compositions for detection of 5-methylcytosine in DNA.

INTRODUCTION

Methylation of cytosine in the 5-position of the pyrimidine ring is an important epigenetic modification found in eukaryotic genomes. In animals, 5-methylcytosine can be found in various locations in a genome, such as in cytosine-guanosine dinucleotide (CpG) motifs. The presence of 5-methylcytosine in a promoter can alter the binding of transcription factors and other proteins, and thereby alter gene expression. In addition, cell transformation to a cancerous state can correlate with changes in the cell's 5-methylcytosine profile. Detection of 5-methylcytosine is, therefore, of importance to both researchers and clinicians.

SUMMARY

Accordingly, the present inventors have developed novel compositions and methods for detecting 5-methylcytosine in nucleic acids.

In various embodiments, the present teachings set forth herein describe a 5-methylcytosine discriminator. A 5-methylcytosine discriminator can comprise a cytosine-pairing moiety, and a moiety which hinders hydrogen bonding between the cytosine-pairing moiety and a 5-methylcytosine. The cytosine pairing moiety can be a moiety that, in the absence of hindrance, can form hydrogen bonds with a cytosine. The cytosine-pairing moiety can be, in some configurations, a guanine moiety. A 5-methylcytosine discriminator can further comprise a 5 carbon sugar moiety, such as a deoxyribose moiety or a dideoxyribose moiety. In addition, a 5-methylcytosine discriminator can further comprise up to three phosphate groups. The phosphate groups can comprise a linear chain attached to a 5' carbon of a 5 carbon sugar comprised by a 5-methylcytosine discriminator. In some embodiments, a 5-methylcytosine discriminator can be a deoxyG*triphosphate (dG*TP) or a dideoxyG*triphosphate (ddG*TP), wherein G* represents a guanine moiety contiguous with a moiety which hinders hydrogen bonding between the guanine and a 5-methylcytosine.

In various configurations, the moiety which hinders hydrogen bonding between the cytosine-pairing moiety and a 5-methylcytosine in a 5-methylcytosine discriminator can be an alkyl moiety, an alkoxy moiety, a sulfur-containing moiety, a nitrogen-containing moiety, a phosphorus-containing moiety or a halogen-containing moiety. In some aspects, the alkyl moiety can be a methyl moiety.

In various configurations, a 5-methylcytosine discriminator can further comprise a linker moiety which can extend between the cytosine-pairing moiety and the moiety which hinders hydrogen bonding between the cytosine-pairing moiety and a 5-methylcytosine. The linker can be a planar linker, and can comprise a plurality of fused rings. The fused rings can comprise, in some aspects, one or more aromatic rings. In various configurations, a plurality of fused rings can comprise from three to about ten fused rings, or from four to about eight fused rings. In some aspects, a plurality of fused rings can comprise three fused rings, or four fused rings.

In various configurations, a cytosine-pairing moiety and a planar linker can be rigidly attached, and, furthermore, can be co-planar. A rigid attachment in some aspects can comprise an amide bond which can extend between the cytosine-pairing moiety and the linker, while in some other aspects a rigid attachment can comprise a carbon-carbon double bond.

In various configurations, a 5-methylcytosine discriminator can comprise a structure such as

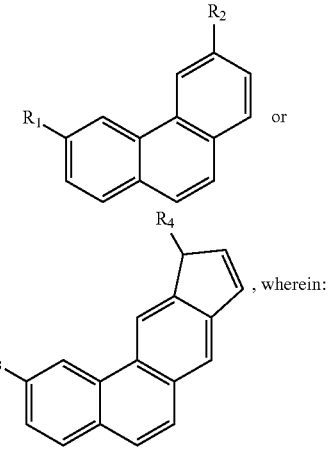

, wherein:

$R_1$ and $R_3$ can each comprise a cytosine-pairing moiety; and $R_2$ and $R_4$ can each comprise a moiety which hinders hydrogen bonding between the cytosine-pairing moiety and a 5-methylcytosine.

In various aspects, one or more carbon atoms at each position within an aromatic ring of the above structures can be substituted with a heteroatom. A heteroatom can be, for example, a nitrogen atom, an oxygen atom, a sulfur atom or a phosphorus atom.

In various configurations, the moiety which hinders hydrogen bonding between the cytosine-pairing moiety and a 5-methylcytosine, and a 5-methyl group of the 5-methylcytosine, can have a calculated distance less than or equal to about 1.6 Angstroms, a calculated distance less than or equal to about 1.2 Angstroms, or a calculated distance less than or equal to about 0.75 Angstroms.

A 5-methylcytosine discriminator of the present teachings can comprise a pentose moiety in some configurations. The pentose moiety can be covalently linked to the cytosine-pairing moiety, for example at a linkage between the 1' carbon of a pentose moiety and a nitrogen atom at the 9 position of a guanosine moiety. The pentose moiety can be, in various aspects, a ribose moiety, a 2'-deoxyribose moiety, or a 2',3'-dideoxyribose moiety.

In some embodiments, a 5-methylcytosine discriminator of the present teachings can comprise the following structure:

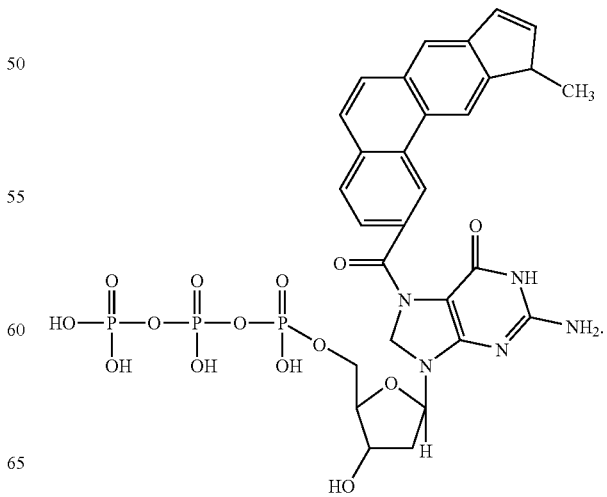

In alternative embodiments, a 5' methylcytosine discriminator can comprise the following structure:

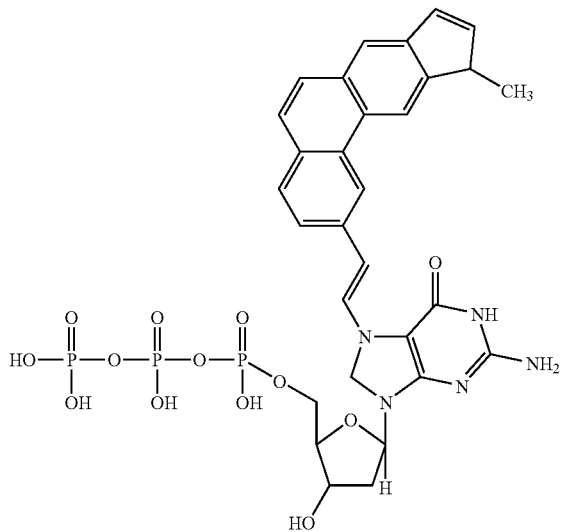

In some configurations of the structure, one or more carbon atoms comprised by a fused aromatic ring can be substituted with a heteroatom, provided that the planarity of the fused rings is maintained. A heteroatom can be, for example, a nitrogen atom, an oxygen atom, a sulfur atom, or a phosphorus atom. Furthermore, in some embodiments, hydrogen atoms attached to an aromatic ring can be substituted with another atom or group, such as, for example, a halogen, a hydroxyl, an amino, carboxylic acid, a sulphate, or a phosphate. In addition, in various configurations, the pentose moiety of the structure can comprise a hydroxyl group substituting for a hydrogen at the 2' carbon.

In various configurations of the structure, a 5-methylcytosine discriminator can comprise a label. A label can be an atom or a moiety which can be detected. In some configurations, a label can be a fluorophore, such as, in non-limiting example, FAM, VIC, Sybra Green, TET, HEX, JOE, NED, LIZ, TAMRA, ROX, ALEXA, Texas Red, Cy3, Cy5, Cy7, Cy9, or dR6G. In some aspects, the fluorophore label can be VIC or FAM. In certain embodiments, a label can be a hapten, such as, in non-limiting example, biotin or digoxygenin. In certain configurations, a label can be an atom such as a radioisotope. Exemplary radioisotopes can be $^{32}P$, $^{33}P$, $^{35}S$, $^{3}H$ and $^{14}C$.

In various embodiments, the present teachings set forth herein describe methods of detecting a 5-methylcytosine comprised by a target nucleic acid. In some embodiments, these methods can comprise forming a detection mixture comprising a DNA polymerase and a hybrid nucleic acid comprising the target nucleic acid hybridized to an primer oligonucleotide. The primer oligonucleotide can comprise a 3' terminal nucleotide base paired with its complement in the target nucleic acid immediately adjacent to a target nucleotide. A target nucleotide can be an unpaired nucleotide, located immediately 5' to the nucleotide base paired with the 3' end nucleotide of the primer oligonucleotide. In various configurations, a method can further comprise adding a 5-methylcytosine discriminator to the detection mixture, and detecting inhibition of hydrogen bond formation between the 5-methylcytosine discriminator and the target nucleotide. In various configurations, detecting inhibition of hydrogen bond formation between the 5-methylcytosine discriminator and the target nucleotide can comprise detecting inhibition of pyrophosphate release from the 5-methylcytosine discriminator, such as a 5-methylcytosine discriminator described herein.

In certain aspects, detecting inhibition of hydrogen bond formation between the 5-methylcytosine discriminator and a target 5-methylcytosine further can comprise adding dGTP or ddGTP to the detection mixture subsequent to the adding of the 5-methylcytosine discriminator, and detecting pyrophosphate release from the dGTP or the ddGTP.

In certain embodiments, detecting a 5-methylcytosine can comprise forming a detection mixture comprising a DNA polymerase and a hybrid nucleic acid comprising the target nucleic acid hybridized to a primer oligonucleotide, the primer oligonucleotide comprising a 3' end nucleotide base paired with its complement in the target nucleic acid immediately adjacent to a target nucleotide; adding a 5-methylcytosine discriminator and dGTP or ddGTP to the detection mixture; and detecting inhibition of hydrogen bond formation between the 5-methylcytosine discriminator and the target nucleotide, wherein detecting inhibition of hydrogen bond formation between the 5-methylcytosine discriminator and the target can comprise detecting elevated incorporation to the primer oligonucleotide of the dGTP or the ddGTP compared to incorporation to the primer oligonucleotide of the 5-methylcytosine discriminator. In these embodiments, a control ratio of incorporation to the primer of .dGTP or ddGTP to 5-methylcytosine discriminator can be established for a cytosine target nucleotide. A ratio of incorporation of dGTP or ddGTP to 5-methylcytosine discriminator which exceeds the control ratio can be indicative of a 5-methyl cytosine target nucleotide, In these embodiments, the 5-methylcytosine discriminator can further comprise a first label. Furthermore, the dGTP or the ddGTP can further comprise a second label which differs from the first label. In some configurations of these embodiments, the first and second labels can each be a fluorophore, a hapten, or a radioisotope, as discussed supra.

In various configurations, a primer oligonucleotide can comprise at least about 10 nucleotides up to about 400 nucleotides; at least about 15 nucleotides up to about 100 nucleotides, or at least about 20 nucleotides up to about 50 nucleotides.

In various configurations, a primer oligonucleotide can comprise a sequence at least about 70% complementary to a contiguous sequence of the target nucleic acid, at least about 80% complementary to a contiguous sequence of the target nucleic acid, at least about 90% complementary to a contiguous sequence of the target nucleic acid, or 100% complementary to a contiguous sequence of the target nucleic acid.

In various embodiments, a method of detecting a 5-methylcytosine can further comprise one or more enzymes that can be used to detect pyrophosphate. An enzyme in these configurations can be, for example, a sulfurylase, a luciferase, or an apyrase.

In some configurations, a 5-methylcytosine discriminator can comprise a cytosine-pairing moiety and a moiety which hinders hydrogen bonding between the cytosine-pairing moiety and a 5-methylcytosine, as described supra. In these configurations, the moiety which hinders hydrogen bonding between the cytosine-pairing moiety and a 5-methylcytosine can be an alkyl moiety such as a methyl moiety. The 5-methylcytosine discriminator can further comprise a planar linker extending between the cytosine-pairing moiety and the moiety which hinders hydrogen bonding between the cytosine-pairing moiety and a 5-methylcytosine. In some aspects, the planar linker can comprise a plurality of fused rings, and the 5-methylcytosine discriminator can further comprise an amide bond extending between the cytosine-pairing moiety and the linker. In various aspects of the methods of the teachings herein, the 5-methylcytosine discriminator can comprise the structure

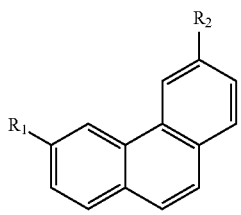

wherein $R_1$ can comprises a cytosine-pairing moiety and $R_2$ can comprise a moiety which hinders hydrogen bonding between the cytosine-pairing moiety and a 5-methylcytosine.

Similarly, in various aspects of the methods taught herein, the 5-methylcytosine discriminator can comprise the structure

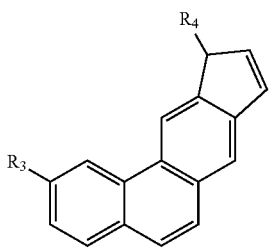

wherein $R_3$ comprises a cytosine-pairing moiety and $R_4$ can comprise a moiety which hinders hydrogen bonding between the cytosine-pairing moiety and a 5-methylcytosine.

In some configurations, a moiety which hinders hydrogen bonding between the cytosine-pairing moiety and a 5-methylcytosine, and a 5-methyl group of the 5-methylcytosine, have a calculated distance less than or equal to about 1.6 Angstroms, less than or equal to about 1.2 Angstroms, or less than or equal to about 0.75 Angstroms.

In various embodiments of methods herein, a cytosine-pairing moiety can be a guanine moiety, and a 5-methylcytosine discriminator can comprise the structure:

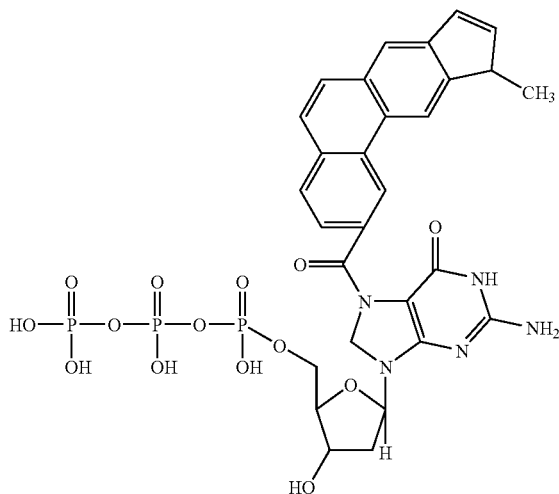

In certain aspects, the connector extending between the guanine and the planar linker can comprise a carbon-carbon double bond instead of an amide bond, and the 5-methylcytosine discriminator can have the following structure:

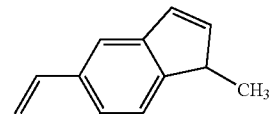

In various embodiments, the present teachings set forth herein describe a kit for detecting 5-methyl cytosine. In certain configurations, a kit can comprise a 5-methylcytosine discriminator, wherein the discriminator comprises a cytosine-pairing moiety and a moiety which hinders hydrogen bonding between the cytosine-pairing moiety and a 5-methylcytosine, and packaging. The 5-methylcytosine discriminator can comprise a cytosine-pairing moiety and a moiety which hinders hydrogen bonding between the cytosine-pairing moiety and a 5-methylcytosine, as described supra. In some configurations, a 5-methylcytosine comprised by a kit can further comprise a label, such as a fluorophore, a hapten, or a radioisotope, as described supra.

In some configurations, a kit can further comprise dGTP or ddGTP. Furthermore, in certain aspects, a dGTP or ddGTP can further comprise a second label. The second label can be a moiety or atom as described supra, although the label for the dGTP or ddGTP can be different from a label comprised by a 5-methylcytosine discriminator.

DESCRIPTION OF VARIOUS EMBODIMENTS

In various embodiments, the present teachings set forth herein describe methods of detecting a 5-methyl cytosine comprised by a target nucleic acid. In some embodiments, these methods can comprise forming a detection mixture comprising a DNA polymerase and a hybrid nucleic acid comprising the target nucleic acid hybridized to an primer oligonucleotide, the primer oligonucleotide comprising a 3' end nucleotide base paired with its complement in the target nucleic acid immediately adjacent to a target nucleotide. A target nucleotide can be an unpaired nucleotide, located immediately 5' to the nucleotide base paired with the 3' end nucleotide of the primer oligonucleotide. In various configurations, a method can further comprise adding a 5-methyl cytosine discriminator to the detection mixture, and detecting inhibition of hydrogen bond formation between the 5-methyl cytosine discriminator and the target nucleotide. In various configurations, detecting inhibition of hydrogen bond formation between the 5-methyl cytosine discriminator and the target nucleotide can comprise detecting inhibition of pyrophosphate released from the 5-methyl cytosine discriminator, such as a 5-methyl cytosine discriminator described herein.

In certain aspects, detecting inhibition of hydrogen bond formation between the 5-methyl cytosine discriminator and target nucleotide further can comprise adding dGTP to the detection mixture subsequent to the adding of the 5-methyl cytosine discriminator, and detecting pyrophosphate release from the dGTP.

In various configurations, a primer oligonucleotide can comprise at least about 10 nucleotides up to about 400 nucleotides; at least about 15 nucleotides up to about 100 nucleotides, or at least about 20 nucleotides up to about 50 nucleotides.

In various configurations, a primer oligonucleotide can comprise a sequence at least about 70% complementary to a contiguous sequence of the target nucleic acid, at least about 80% complementary to a contiguous sequence of the target nucleic acid, at least about 90% complementary to a contiguous sequence of the target nucleic acid, or 100% complementary to a contiguous sequence of the target nucleic acid.

In various embodiments, a method of detecting a 5-methyl cytosine can further comprise one or more enzymes that can be used to detect pyrophosphate, such as pyrophosphate released from a 5-methyl cytosine discriminator described herein. An enzyme in these configurations can be, for example, a sulfurylase, a luciferase, or an apyrase.

In some configurations, a 5-methyl cytosine discriminator can comprise a cytosine-pairing moiety and a moiety which hinders hydrogen bonding between the cytosine-pairing moiety and a 5-methyl cytosine, as described supra. In these configurations, the moiety which hinders hydrogen bonding between the cytosine-pairing moiety and a 5-methyl cytosine can be an alkyl moiety such as a methyl moiety. The 5-methyl cytosine discriminator can further comprise a planar linker extending between the cytosine-pairing moiety and the moiety which hinders hydrogen bonding between the cytosine-pairing moiety and a 5-methyl cytosine. In some aspects, the planar linker can comprise a plurality of fused rings, and the 5-methyl cytosine discriminator can further comprise an amide bond extending between the cytosine-pairing moiety and the linker. In various aspects of the methods of the teachings herein, the 5-methyl cytosine discriminator can comprise the structure

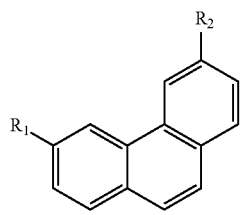

wherein $R_1$ can comprises a cytosine-pairing moiety and $R_2$ can comprise a moiety which hinders hydrogen bonding between the cytosine-pairing moiety and a 5-methyl cytosine.

Similarly, in various aspects of the methods taught herein, the 5-methyl cytosine discriminator can comprise the structure

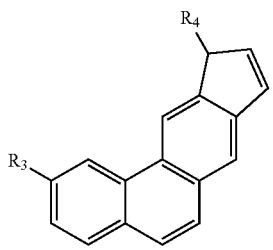

wherein $R_3$ comprises a cytosine-pairing moiety and $R_4$ can comprise a moiety which hinders hydrogen bonding between the cytosine-pairing moiety and a 5-methyl cytosine.

In some configurations, a moiety which hinders hydrogen bonding between the cytosine-pairing moiety and a 5-methyl cytosine, and a 5-methyl group of the 5-methyl cytosine, have a calculated distance less than or equal to about 1.6 Angstroms, less than or equal to about 1.2 Angstroms, or less than or equal to about 0.75 Angstroms.

In various embodiments of methods herein, a cytosine-pairing moiety can be a guanine moiety, and a 5-methyl cytosine discriminator can comprise the structure:

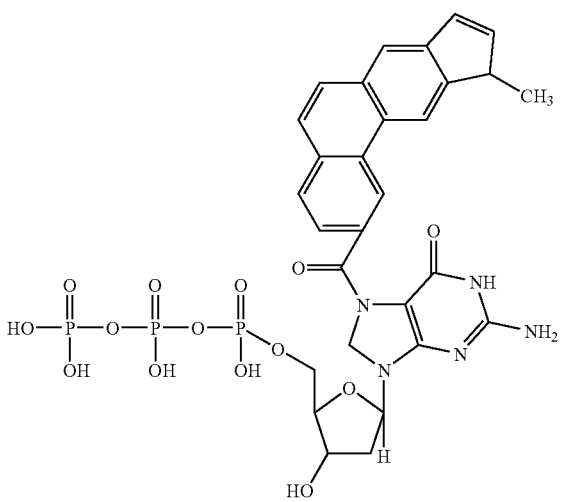

In certain aspects, the connector extending between the guanine and the planar linker can comprise a carbon-carbon double bond instead of an amide bond, and the 5-methyl cytosine discriminator can have the following structure:

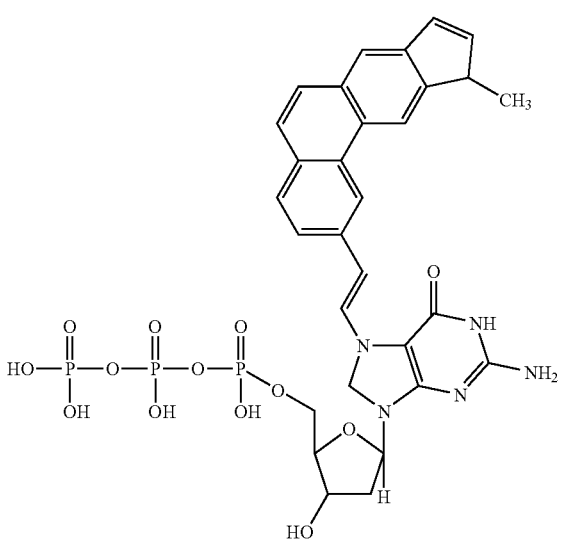

can use methods modified from sequencing methods disclosed in U.S. Pat. Nos. 6,210,891 and 6,258,568 to Nyren, which are hereby incorporated by reference in their entireties. In these embodiments, methods

DETAILED DESCRIPTION

The methods described herein utilize laboratory techniques well known to skilled artisans and can be found in laboratory manuals such as Sambrook et al., Molecular Cloning: A Laboratory Manual, 3rd ed. Cold Spring Harbor Laboratory Press, Cold Spring Harbor, N.Y., 2001. Methods for organic synthesis of molecules described herein can be found in textbooks such as Pine et al., Organic Chemistry, 4th Ed., McGraw-Hill, 1980.

The present inventors have developed novel compositions and methods for detecting 5-methylcytosine in nucleic acids. In various embodiments, the present teachings set forth herein describe a 5-methylcytosine discriminator. A 5-methylcytosine discriminator can comprise a cytosine-pairing moiety, and a moiety which hinders hydrogen bonding between the cytosine-pairing moiety and a 5-methylcytosine. The cytosine-pairing moiety can be a moiety that, in the absence of hindrance, can form hydrogen bonds with a cytosine. The hydrogen bonds formed between a cytosine and a cytosine-pairing moiety, can be hydrogen bonds of Watson-Crick base pairs. A cytosine-pairing moiety can be, in some configurations, a guanine moiety. In various configurations, 5-methylcytosine discriminator can further comprise a 5 carbon sugar moiety, such as a deoxyribose moiety or a dideoxyribose moiety. As used herein, reference to a deoxyribose moiety can be also considered to include a dideoxyribose moiety unless indicated otherwise. For example, any reference to a dGTP can also be considered a reference to a ddGTP.

In various configurations, a 5-methylcytosine discriminator can further comprise up to three phosphate groups. The phosphate groups can comprise a linear chain attached to a 5' carbon of a 5 carbon sugar comprised by a 5-methylcytosine discriminator. The linear chain can comprise three phosphate groups. Hence, in some embodiments, a 5-methylcytosine discriminator can be a deoxyG*triphosphate (dG*TP), wherein G* represents a guanine moiety contiguous with a moiety which hinders hydrogen bonding between the guanine moiety and a 5-methylcytosine.

In various embodiments, a moiety which hinders hydrogen bonding can be a moiety that sterically interferes with hydrogen bonding, such as a moiety that can be predicted to be positioned close to or overlapping the position of the 5-methyl group in a theoretical base pairing between the cytosine-pairing moiety and a 5-methylcytosine. A position that is close to or overlapping that of the 5-methyl group of a 5-methylcytosine can have a predicted distance from the methyl group that is less than or equal to about 1.6 Angstroms, less than or equal to about 1.2 Angstroms, or less than or equal to about 0.75 Angstroms. Such distances can be determined using molecular modeling methods well known to skilled artisans. In some configurations, theoretical interatomic distances can be calculated with the aid of a digital computer and supporting software for molecular modeling, such as, for example, HyperChem 7.5 software (Hypercube, Inc.). Without being limited by theory, it is believed that theoretical intermolecular distances less than or equal to about 1.6 Angstroms, less than or equal to about 1.2 Angstroms, or less than or equal to about 0.75 Angstroms can indicate steric hindrance between molecules. In the present case, it is believed that the theoretical position of a 5-methylcytosine discriminator based paired with a 5-methylcytosine nucleotide would be sterically hindered, precluding actual base pairing. Because base pairing with a 5-methylcytosine is precluded, a DNA polymerase cannot incorporate the discriminator to form a nucleotide base paired with a 5-methylcytosine target base. However, base pairing of the discriminator with a cytosine nucleotide is not precluded, and a DNA polymerase can incorporate the discriminator to form a base pair with a cytosine nucleotide.

In various configurations, the moiety which hinders hydrogen bonding between the cytosine-pairing moiety and a 5-methylcytosine in a 5-methylcytosine discriminator can be an alkyl moiety, an alkoxy moiety, a sulfur-containing moiety such as a sulfate or a sulfhydryl; a nitrogen-containing moiety such as a nitrate, a nitroso or an amine; a phosphorus-containing moiety such as a phosphate, or a halogen-containing moiety, such as a fluorine atom, a chlorine atom, a bromine atom or a iodine atom. In some aspects, the alkyl moiety can be a $C_1$ to $C_{10}$ alkyl moiety, such as, for example, a methyl moiety.

In various configurations, a 5-methylcytosine discriminator can further comprise a linker moiety which can extend between the cytosine-pairing moiety and the moiety which hinders hydrogen bonding between the cytosine-pairing moiety and a 5-methylcytosine. The linker can be a substantially planar linker, and can comprise, in various configurations, a plurality of fused rings. The fused rings can comprise, in some aspects, one or more aromatic rings. In various configurations, a plurality of fused rings can comprise from three to about ten fused rings, or from four to about eight fused rings. In some aspects, a plurality of fused rings can comprise three fused rings, or four fused rings.

In various configurations, a cytosine-pairing moiety and a planar linker can be rigidly attached, and, furthermore, can be co-planar. A rigid attachment in some aspects can comprise an amide bond which can extend between the cytosine-pairing moiety and the linker, while in some other aspects a rigid attachment can comprise a carbon-carbon double bond. Without being limited by theory, it is expected that an amide bond or a carbon-carbon double bond comprised by a discriminator can be sufficiently rigid such that the cytosine-pairing moiety, the linker and the moiety which hinders hydrogen bonding together form a rigid structure which sterically hinders base pairing with a 5-methylcytosine.

In various configurations, a 5-methylcytosine discriminator can comprise a structure such as

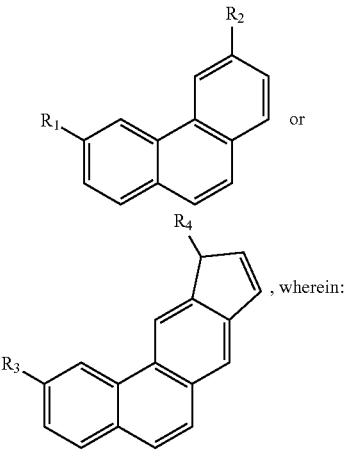

, wherein:

$R_1$ and $R_3$ can each comprise a cytosine-pairing moiety; and $R_2$ and $R_4$ can each comprise a moiety which hinders hydrogen bonding between the cytosine-pairing moiety and a 5-methylcytosine.

In various aspects, one or more carbon atoms at each position within an aromatic ring of the above structures can be substituted with a heteroatom. A heteroatom can be, for example, a nitrogen atom, an oxygen atom, a sulfur atom or a phosphorus atom. Furthermore, hydrogen atoms attached to an aromatic ring can be substituted with another atom or group, such as, for example, a halogen, a hydroxyl, an amino, carboxylic acid, a sulphate, or a phosphate. Such substitutions can retain the overall structure of the discriminator such that it retains its properties of hindering base pairing with a 5-methyl, while changing other properties of the discriminator. For example, substitution of one or more hydrogens with a hydroxy group can increase the aqueous solubility of a discriminator.

A 5-methylcytosine discriminator of the present teachings can comprise a pentose moiety in some configurations. The pentose moiety can be covalently linked to the cytosine-pairing moiety, for example at a linkage between the 1' carbon of a pentose moiety and a nitrogen atom at the 9 position of a guanosine moiety. The pentose moiety can be, in various aspects, a ribose moiety, a 2'-deoxyribose moiety, or a 2',3'-dideoxyribose moiety.

In some configurations, a 5-methylcytosine discriminator of the present teachings can comprise the following structure:

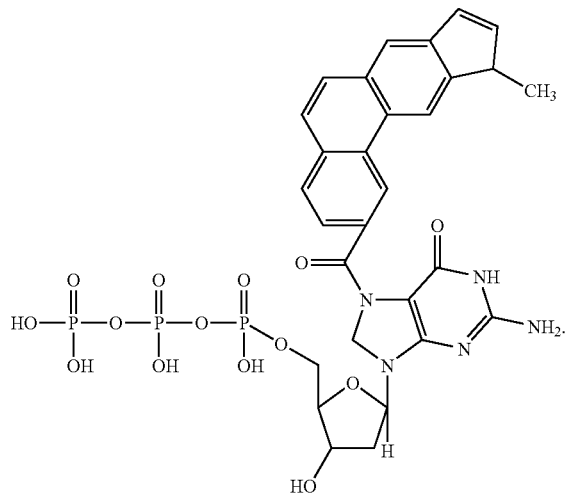

In certain alternative configurations, a 5' methylcytosine discriminator can comprise the following structure:

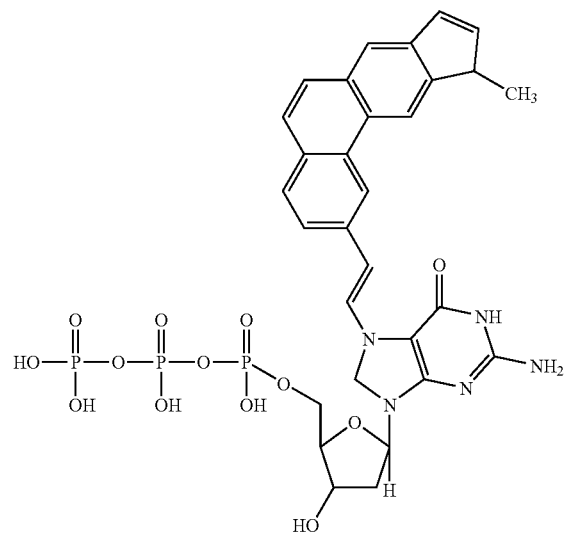

In some configurations of the structure, one or more carbon atoms comprised by a fused aromatic ring can be substituted with a heteroatom, provided that the planarity of the fused rings is maintained. A heteroatom can be, for example, a nitrogen atom, an oxygen atom, a sulfur atom, or a phosphorus atom. Furthermore, hydrogen atoms attached to an aromatic ring can be substituted with another atom or group, such as, for example, a halogen, a hydroxyl, an amino, carboxylic acid, a sulphate, or a phosphate. In addition, in various configurations, the pentose moiety of the structure can comprise a hydroxyl group substituting for a hydrogen at the 2' carbon, so that the pentose moiety can be a deoxyribose.

In various configurations of the structure, a 5-methylcytosine discriminator can comprise a label. A label can be an atom or a moiety which can be detected. The detection can be direct or indirect. For example, in some configurations, a label can be a fluorophore, such as, in non-limiting example, FAM, VIC, Sybra Green, TET, HEX, JOE, NED, LIZ, TAMRA, ROX, ALEXA, Texas Red, Cy3, Cy5, Cy7, Cy9, or dR6G. In some aspects, the fluorophore label can be VIC or FAM. In certain embodiments, a label can be a hapten, such as, in non-limiting example, biotin or digoxygenin. A hapten can be detected with a probe, such as a binding partner for the hapten. A binding partner for the hapten can be, for example, an antibody directed against the hapten, such as, for example, an anti-biotin antibody or an anti-digoxygenin antibody, or a biotin binding partner such as avidin or streptavidin. A binding partner can serve as a probe for detecting a hapten label. Detection of binding can comprise any known technique, such as, for example, direct or indirect immunofluorescence or radioimmunoassay. In certain configurations, a label can be a radioisotope, such as, for example, $^{32}P$, $^{33}P$, $^{35}S$, $^{3}H$ and $^{14}C$. A radioisotope label can be detected using methods well known to skilled artisans, such as, for example, scintillation counting.

In various embodiments, the present teachings set forth herein describe methods of detecting a 5-methylcytosine comprised by a target nucleic acid. In some embodiments, these methods can comprise forming a detection mixture comprising a DNA polymerase and a hybrid nucleic acid comprising the target nucleic acid hybridized to an primer oligonucleotide. The primer oligonucleotide can comprise a 3' terminal nucleotide base paired with its complement in the target nucleic acid immediately adjacent to a target nucleotide. A target nucleotide can be an unpaired nucleotide, located immediately 5' to the nucleotide base paired with the 3' end nucleotide of the primer oligonucleotide. In various configurations, a method can further comprise adding a 5-methylcytosine discriminator to the detection mixture, and detecting inhibition of hydrogen bond formation between the 5-methylcytosine discriminator and the target nucleotide. In various configurations, detecting inhibition of hydrogen bond formation between the 5-methylcytosine discriminator and the target nucleotide can comprise detecting inhibition of pyrophosphate release from the 5-methylcytosine discriminator, such as a 5-methylcytosine discriminator described herein.

In certain aspects, detecting inhibition of hydrogen bond formation between the 5-methylcytosine discriminator and target nucleotide further can comprise adding dGTP or ddGTP to the detection mixture subsequent to the adding of the 5-methylcytosine discriminator, and detecting pyrophosphate release from the dGTP or ddGTP. Hence, detection of a 5' methylcytosine at a target nucleotide can comprise an initial failure to detect incorporation of the discriminator such as a dG*TP, followed by subsequent detection of incorporation of a guanosine.

In certain embodiments, detecting a 5-methylcytosine can comprise forming a detection mixture comprising a DNA polymerase and a hybrid nucleic acid comprising the target nucleic acid hybridized to a primer oligonucleotide, the primer oligonucleotide comprising a 3' end nucleotide base paired with its complement in the target nucleic acid immediately adjacent to a target nucleotide; adding a 5-methylcytosine discriminator and dGTP or ddGTP to the detection mixture; and detecting inhibition of hydrogen bond formation between the 5-methylcytosine discriminator and the target nucleotide, wherein detecting inhibition of hydrogen bond formation between the 5-methylcytosine discriminator and the target can comprise detecting elevated incorporation to the primer oligonucleotide of the dGTP or the ddGTP compared to incorporation to the primer oligonucleotide of the 5-methylcytosine discriminator. In these embodiments, a control ratio of incorporation to the primer of .dGTP or ddGTP to 5-methylcytosine discriminator can be established for a cytosine target nucleotide. A ratio of incorporation of dGTP or ddGTP to 5-methylcytosine discriminator which exceeds the control ratio can be indicative of a 5-methyl cytosine target nucleotide, Hence, for example, in some configurations of these embodiments, a molar ratio of incorporation of dGTP to incorporation of dG*TP can be determined for a cytosine target nucleotide. For example, a molar ratio can be about 1:1 for incorporation to a primer when the target nucleotide is a cytosine. However, if the target nucleotide is a 5-methylcytosine, the molar ratio of incorporation of dGTP to dG*TP can be, for example, at least about 1000:1, or greater.

In these embodiments, the 5-methylcytosine discriminator can further comprise a first label. Furthermore, the dGTP or the ddGTP can further comprise a second label which differs from the first label. In some configurations of these embodiments, the first and second labels can each be a fluorophore, a hapten, or a radioisotope, as discussed supra. In non-limiting example, a dGTP can comprise a first fluorophore such as VIC, and a dG*TP 5-methylcyotisine discriminator can comprise a second fluorophore such as FAM. Incorporation can be detected using methods and equipment well known to skilled artisans. Incorporation of both fluorophores in approximately equimolar amounts can be indicative of a cytosine at the target nucleotide, whereas incorporation of VIC only, or at a molar amount at least hundreds or thousands fold greater than incorporation of FAM, can be indicative of a 5-methylcytosine at the target nucleotide. In various configurations, extent of incorporation of each label can be calibrated using controls, so that, for example, a dGTP can comprise a radioisotope label and can be used in conjunction with a dG*TP comprising a fluorophore label.

In various configurations, a primer oligonucleotide can comprise at least about 10 nucleotides up to about 400 nucleotides; at least about 15 nucleotides up to about 100 nucleotides, or at least about 20 nucleotides up to about 50 nucleotides.

In various configurations, a primer oligonucleotide can comprise a sequence at least about 70% complementary to a contiguous sequence of the target nucleic acid, at least about 80% complementary to a contiguous sequence of the target nucleic acid, at least about 90% complementary to a contiguous sequence of the target nucleic acid, or 100% complementary to a contiguous sequence of the target nucleic acid.

In various embodiments, a detection mixture of the present methods can further comprise one or more enzymes that can be used to detect pyrophosphate released from a nucleotide precursor such as a dGTP or a dG*TP. An enzyme in these configurations can be, for example, a sulfurylase, a luciferase, or an apyrase. In various embodiments, methods for detection of pyrophosphate released during nucleotide incorporation can be methods disclosed in U.S. Pat. Nos. 6,210,891 and 6,258,568 to Nyren, which are hereby incorporated by reference in their entireties. These methods can be Pyrosequencing™ methods, for which enzymes and reagents are made available commercially by Pyrosequencing, Inc. Briefly, in these methods, a target nucleotide situated in a target nucleic acid, immediately adjacent to a nucleotide base paired with the 3' end of a primer oligonucleotide can be determined by detecting incorporation of its base pairing partner by a DNA polymerase. Incorporation can be detected by detecting pyrophosphate released by the DNA polymerase. For example, if the target nucleotide is an adenine, introduction of dTTP to a mixture comprising the target nucleic acid and a primer oligonucleotide will cause release of pyrophosphate. The pyrophosphate can be detected using methods such as detection methods disclosed in these patents. Detection of pyrophosphate can involve in some configurations generation of ATP that incorporates released pyrophosphate, followed by biochemiluminescent detection of the ATP generated. For example, ATP can be detected and quantified by photon emission using an ATP-dependent luciferase such as a firefly luciferase and a luciferin, using methods and equipment well known to skilled artisans.

In various embodiments, the present teachings set forth herein describe a kit for detecting 5-methyl cytosine. In certain configurations, a kit can comprise a 5-methylcytosine discriminator, wherein the discriminator comprises a cytosine-pairing moiety and a moiety which hinders hydrogen bonding between the cytosine-pairing moiety and a 5-methylcytosine, and packaging. The 5-methylcytosine discriminator can comprise a cytosine-pairing moiety and a moiety which hinders hydrogen bonding between the cytosine-pairing moiety and a 5-methylcytosine, as described supra. In some configurations, a 5-methylcytosine discriminator comprised by a kit can be a dG*TP as described supra. Furthermore, a 5-methylcytosine discriminator comprised by a kit can further comprise a label, such as, for example, a fluorophore, a hapten, or a radioisotope, as described supra.

In some configurations, a kit can further comprise dGTP or ddGTP. In certain aspects, a dGTP or ddGTP can further comprise a second label. The second label can be a moiety or atom as described supra, although the label for the dGTP or ddGTP can be different from a label comprised by a 5-methylcytosine discriminator. In a non-limiting example, a kit can comprise a dG*TP tagged with a fluorophore such as VIC; the kit can further comprise a dGTP tagged with a fluorophore such as FAM. In various configurations, a kit can also comprise instructions, as well as other nucleoside triphosphates such as dATP, dGTP and dTTP.

EXAMPLES

Aspects of the present teachings may be further understood in light of the following examples, which should not be construed as limiting the scope of the present teachings in any way. Use of the past tense in these Examples is not to be understood as an indication that any described event actually occurred or that any reported results were actually achieved.

Example 1

This example illustrates determination of a sequence comprising a 5-methylcytosine.

In this example, a genomic DNA comprises the sequence 5'-GAmeCGCGATAATATTAGATCCGACGAC-3' (SEQ ID NO: 1). To identify the 5-methylcytosine in the sequence, a primer complementary to GATCCGACGAC (SEQ ID NO: 2), i.e., GTCGTCGGATC (SEQ ID NO: 3) is hybridized to the genomic DNA. A DNA polymerase and dNTPs are cyclically added in the order dATP, dCTP, dG*TP, dGTP and dTTP, wherein dG*TP is the 5-methylcytosine discriminator. In this example, none of the dNTPs are ddNTPs. In the first cycle, no pyrophosphate is detected following addition of dATP, dCTP, dG*TP or dGTP. However, upon addition of dTTP, pyrophosphate is released, which is detected using a photon detector. This reaction indicates that the target nucleotide immediately adjacent to the 3' end of the nucleotide base-paired with the 3' end of the primer is an adenine. The 3' end of the primer now comprises a thymine. Excess dNTPs are removed between cycles using enzymatic methods. In the next cycle, photon emission is detected following addition of dATP. However, the quantity of photons emitted is approximately twice that of the first cycle, indicating that the nucleotide immediately adjacent to the 3'-terminal thymine is an adenine, and that its nearest neighbor is also an adenine. Twelve subsequent cycles indicate incorporation, in order, of TAATATTATCGC (SEQ ID NO: 4) into the primer. Until this point, pyrophosphate has been released from the 5methylcytosine discriminator, because any cytosine was base-paired with a dG*TP. However, during the next cycle, wherein the target nucleotide is a 5-methylcytosine, dG*TP does not form a base pair, and no pyrophosphate is released upon addition of the dG*TP. However, the 5-methylcytosine can form a base pair with dGTP, so that pyrophosphate is released upon addition of dGTP. The release of pyrophosphate upon addition of dGTP but not dG*TP indicates that the target nucleotide is a 5-methylcytosine.

Example 2

This example illustrates determination of a sequence comprising a 5-methylcytosine.

In this example, a genomic DNA comprises the sequence 5'-CGmeCGCGATAAAGATCCGACGAG-3' (SEQ ID NO: 5). To identify the 5-methylcytosine in the sequence, a primer complementary to GATCCGACGAC (SEQ ID NO: 6), i.e., CTCGTCGGATC (SEQ ID NO: 7) is hybridized to the genomic DNA. A DNA polymerase and dNTPs are added in the order dCTP, dG*TP, dTTP, DATP and dGTP. In this example, none of the dNTPs are ddNTPs. In the first cycle, no pyrophosphate is detected until a photon detector reports emission of photons upon addition of dTTP. These results indicate that the target nucleotide immediately adjacent to the 3' end of the nucleotide base-paired with the 3' end of the primer is an adenine. The 3' end of the primer now comprises a thymine. Excess dNTPs are removed between cycles using enzymatic methods. In the next cycle, photon emission is detected following addition of dATP. However, the quantity of photons emitted is approximately one third that of the first cycle, indicating that three thymines were incorporated into the primer in the first cycle, and, therefore, that the target nucleic acid comprised the sequence AAA. Five subsequent cycles indicate incorporation, in order, of ATCGC into the primer. Until this point, pyrophosphate has been released from the 5methylcytosine discriminator, because any cytosine has been base-paired with a dG*TP. However, during the next cycle, wherein the target nucleotide is a 5-methylcytosine, dG*TP does not form a base pair, and no pyrophosphate is released upon addition of the dG*TP. However, the 5-methylcytosine can form a base pair with dGTP, so that pyrophosphate is released upon addition of dGTP. The release of pyrophosphate upon addition of dGTP but not dG*TP indicates that the target nucleotide is a 5-methylcytosine.

All references cited in this specification are hereby incorporated by reference. Any discussion of references cited herein is intended merely to summarize the assertions made by their authors and no admission is made that any reference or portion thereof constitutes relevant prior art. Applicants reserve the right to challenge the accuracy and pertinency of the cited references.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of detecting 5-methylcytosine comprised by a target nucleic acid, the method comprising:
    a) forming a detection mixture comprising a DNA polymerase and a hybrid nucleic acid comprising the target nucleic acid hybridized to a primer oligonucleotide, the primer oligonucleotide comprising a 3' end nucleotide base paired with its complement in the target nucleic acid immediately adjacent to a target nucleotide;
    b) adding a 5-methylcytosine discriminator to the detection mixture; and
    c) detecting inhibition of hydrogen bond formation between the 5-methylcytosine discriminator and the target nucleotide, presence of the inhibition of hydrogen bond formation being indicative of 5-methylcytosine.

2. A method of detecting 5-methylcytosine according to claim 1, wherein detecting inhibition of hydrogen bond formation between the 5-methylcytosine discriminator and target nucleotide comprises detecting inhibition of pyrophosphate release from the 5-methylcytosine discriminator.

3. A method of detecting 5-methylcytosine according to claim 2, wherein detecting inhibition of hydrogen bond formation between the 5-methylcytosine discriminator and target nucleotide further comprises adding dGTP to the detection mixture subsequent to the adding of 5-methylcytosine discriminator, and detecting pyrophosphate release from the dGTP.

4. A method of detecting 5-methylcytosine according to claim 1, wherein the primer oligonucleotide comprises at least about 10 nucleotides up to about 400 nucleotides.

5. A method of detecting 5-methylcytosine according to claim 1, wherein the primer oligonucleotide comprises at least about 15 nucleotides up to about 100 nucleotides.

6. A method of detecting 5-methylcytosine according to claim 1, wherein the primer oligonucleotide comprises at least about 20 nucleotides up to about 50 nucleotides.

7. A method of detecting 5-methylcytosine according to claim 1, wherein the primer oligonucleotide is at least about 70% complementary to a contiguous sequence of the target nucleic acid.

8. A method of detecting 5-methylcytosine according to claim 1, wherein the detection mixture further comprises a sulfurylase, a luciferase, and an apyrase.

9. A method of detecting 5-methylcytosine according to claim 1, wherein the 5-methylcytosine discriminator comprises a cytosine-pairing moiety and a moiety which hinders hydrogen bonding between the cytosine-pairing moiety and a 5-methylcytosine.

10. A method of detecting 5-methylcytosine according to claim 9, wherein the moiety which hinders hydrogen bonding between the cytosine-pairing moiety and a 5-methylcytosine is an alkyl moiety.

11. A method of detecting 5-methylcytosine according to claim 10, wherein the alkyl moiety is a methyl moiety.

12. A method of detecting 5-methylcytosine according to claim 9, wherein the 5-methylcytosine discriminator further comprises a planar linker extending between the cytosine-pairing moiety and the moiety which hinders hydrogen bonding between the cytosine-pairing moiety and a 5-methylcytosine.

13. A method of detecting 5-methylcytosine according to claim 12, wherein the planar linker comprises a plurality of fused rings.

14. A method of detecting 5-methylcytosine according to claim 12, wherein the 5-methylcytosine discriminator further comprises an amide bond extending between the cytosine-pairing moiety and the planar linker.

15. A method of detecting 5-methylcytosine according to claim 12, wherein the 5-methylcytosine discriminator comprises the structure

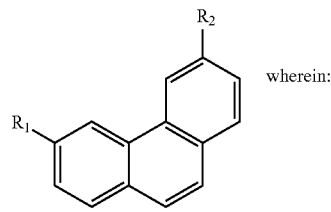

wherein:

R₁ comprises a cytosine-pairing moiety; and

R₂ comprises a moiety which hinders hydrogen bonding between the cytosine-pairing moiety and a 5-methylcytosine.

16. A method of detecting 5-methylcytosine according to claim 12, wherein the 5-methylcytosine discriminator comprises the structure

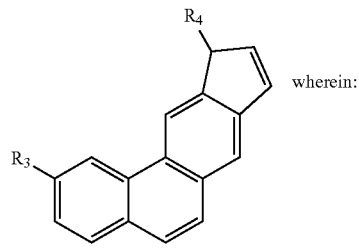

wherein:

R₃ comprises a cytosine-pairing moiety; and

R₄ comprises a moiety which hinders hydrogen bonding between the cytosine-pairing moiety and a 5-methylcytosine.

17. A method of detecting 5-methylcytosine according to claim 9, wherein the moiety which hinders hydrogen bonding between the cytosine-pairing moiety and a 5-methylcytosine, and a 5-methyl group of the 5-methylcytosine, have a calculated distance less than or equal to about 1.6 Angstroms.

18. A method of detecting 5-methylcytosine according to claim 9, wherein the moiety which hinders hydrogen bonding between the cytosine-pairing moiety and a 5-methylcytosine, and a 5-methyl group of the 5-methylcytosine, have a calculated distance less than or equal to about 1.2 Angstroms.

19. A method of detecting 5-methylcytosine according to claim 9, wherein the moiety which hinders hydrogen bonding between the cytosine-pairing moiety and a 5-methylcytosine, and a 5-methyl group of the 5-methylcytosine, have a calculated distance less than or equal to about 0.75 Angstroms.

20. A method of detecting 5-methylcytosine according to claim 9, wherein the cytosine-pairing moiety is a guanine moiety.

21. A method of detecting 5-methylcytosine according to claim 12, wherein the 5-methylcytosine discriminator comprises the structure:

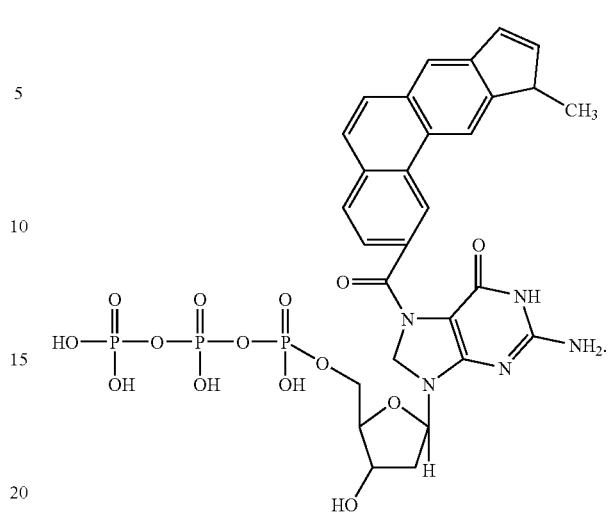

22. A method of detecting 5-methylcytosine according to claim 12, wherein the 5-methylcytosine discriminator comprises the structure:

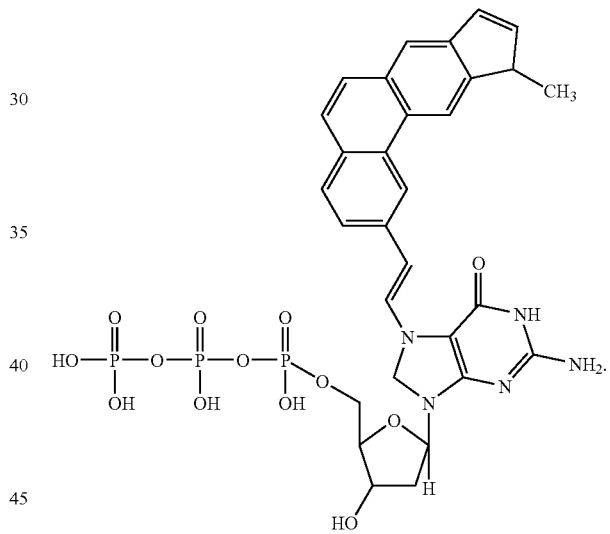

23. A method of detecting 5-methylcytosine according to claim 1, further comprising adding a dGTP or a ddGTP to the detection mixture, and wherein detecting inhibition of hydrogen bond formation between the 5-methylcytosine discriminator and the target nucleotide comprises detecting an elevated incorporation to the primer oligonucleotide of the dGTP or the ddGTP compared to incorporation to the primer oligonucleotide of the 5-methylcytosine discriminator.

24. A method of detecting 5-methylcytosine according to claim 23, wherein the 5-methylcytosine discriminator comprises a first label, and the dGTP or the ddGTP further comprises a second label different from the first label.

25. A method of detecting 5-methylcytosine according to claim 24, wherein the first label and the second label are each selected from the group consisting of a fluorophore, a hapten and a radioisotope.

26. A method of detecting 5-methylcytosine according to claim 25, wherein the fluorophore is selected from the group consisting of FAM, VIC, Sybra Green, TET, HEX, JOE, NED, LIZ, TAMRA, ROX, ALEXA, Texas Red, Cy3, Cy5, Cy7, Cy9, and dR6G.

27. A method of detecting 5-methylcytosine according to claim 26, wherein the fluorophore is VIC or FAM.

28. A method of detecting 5-methylcytosine according to claim 24, wherein at least one of the first label and the second label is a hapten selected from biotin and digoxygenin.

29. A method of detecting 5-methylcytosine according to claim 24, wherein at least one of the first label and the second label is a radioisotope selected from $^{32}P$, $^{33}P$, $^{35}S$, $^{3}H$ and $^{14}C$.

* * * * *